United States Patent [19]

Blette

[11] Patent Number: 5,386,928
[45] Date of Patent: Feb. 7, 1995

[54] DUAL COLLAPSIBLE TUBE DISPENSING ASSEMBLY

[75] Inventor: Russell E. Blette, Hastings, Minn.

[73] Assignee: Minnesota Mining and Manufacturing Company, St. Paul, Minn.

[21] Appl. No.: 152,739

[22] Filed: Nov. 15, 1993

[51] Int. Cl.6 .................................... B65D 35/22
[52] U.S. Cl. .................... 222/94; 222/136; 222/327
[58] Field of Search .......... 222/135, 136, 137, 145, 222/386, 129, 94, 105, 325–327

[56] References Cited

U.S. PATENT DOCUMENTS

| | | | |
|---|---|---|---|
| 2,589,743 | 3/1952 | Snaith | 222/145 X |
| 2,661,870 | 12/1953 | Huenergardt | 222/129 |
| 3,178,157 | 4/1965 | Cole, III | 222/145 X |
| 3,187,951 | 6/1965 | Hardman et al. | 222/135 X |
| 3,223,289 | 12/1965 | Bouet | 222/135 X |
| 3,323,682 | 6/1967 | Creighton, Jr. et al. | 222/94 |
| 3,347,420 | 10/1967 | Donoghue | 222/129 |
| 3,581,399 | 6/1971 | Dragan | 32/60 |
| 3,608,782 | 9/1971 | Sathicq | 222/136 X |
| 4,260,077 | 4/1981 | Schroeder | 222/137 |
| 4,279,362 | 7/1981 | Pursell | 222/136 X |
| 4,340,154 | 7/1982 | VanManen | 222/94 |
| 4,386,717 | 6/1983 | Koob | 222/94 |
| 4,493,436 | 1/1985 | Brokaw | 222/137 X |
| 4,538,920 | 9/1985 | Drake | 366/177 |
| 4,676,657 | 6/1987 | Botrie | 366/177 |
| 4,735,509 | 4/1988 | Rausch | 222/145 X |
| 4,801,008 | 1/1989 | Rich | 222/137 X |
| 4,854,482 | 8/1989 | Bergner | 222/135 X |
| 4,984,715 | 1/1991 | Green | 222/129 |
| 5,052,590 | 10/1991 | Ratcliff | 222/129 X |
| 5,152,432 | 10/1992 | De Laforcade | 222/145 |
| 5,161,715 | 11/1992 | Giannuzzi | 222/82 |
| 5,184,757 | 2/1993 | Giannuzzi | 222/82 |
| 5,242,082 | 9/1993 | Giannuzzi | 222/82 |
| 5,273,190 | 12/1993 | Lund | 222/83 |
| 5,301,835 | 4/1994 | Fulks et al. | 222/105 X |
| 5,301,842 | 4/1994 | Ritter | 222/137 |
| 5,318,203 | 6/1994 | Iaia et al. | 222/94 |
| 5,330,079 | 7/1994 | Keller | 222/135 |
| 5,332,122 | 7/1994 | Herold et al. | 222/105 |

FOREIGN PATENT DOCUMENTS

| | | | |
|---|---|---|---|
| 2248820 | 4/1992 | United Kingdom | 222/145 |
| 9105731 | 5/1991 | WIPO | 222/137 |

*Primary Examiner*—Andres Kashnikow
*Assistant Examiner*—Kenneth DeRosa
*Attorney, Agent, or Firm*—Gary L. Griswold; Walter N. Kirn; James D. Christoff

[57] ABSTRACT

A system for dispensing materials made of two components includes a side-by-side pair of collapsible tubes that fit within a barrel of a pressurized air applicator. As air is admitted into the barrel, the tubes simultaneously collapse to direct components in the tubes through outlet ports and into a static mixer where the components are mixed to a homogeneous mass. Each tube includes a relatively rigid front and rear end piece, and the end pieces are coupled together by pin elements for ease of handling and to facilitate dispensing.

11 Claims, 5 Drawing Sheets

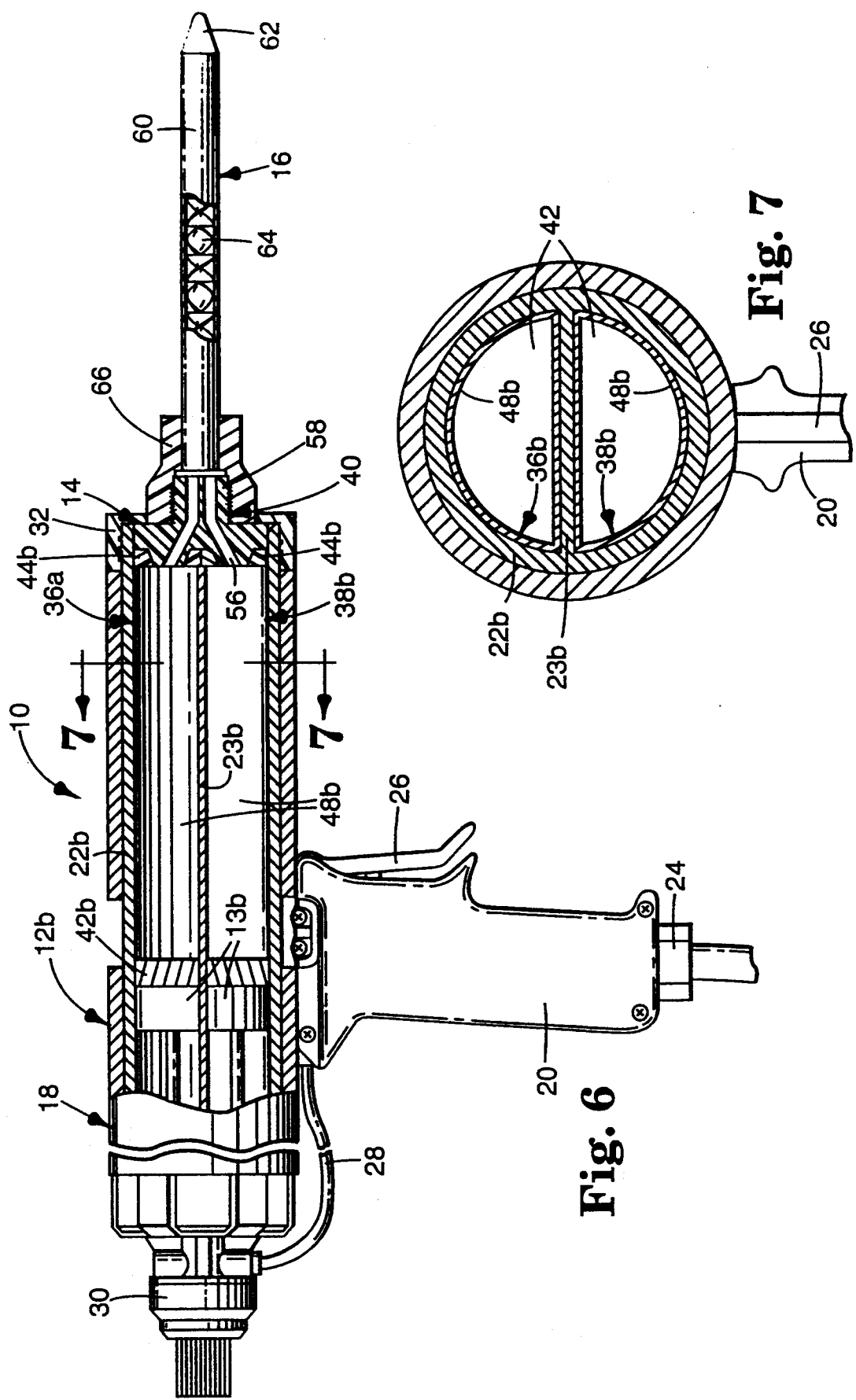

DUAL COLLAPSIBLE TUBE DISPENSING ASSEMBLY

BACKGROUND OF THE INVENTION

1. Field of the Invention

This invention relates to a dispensing assembly that includes a side-by-side pair of tubes for storing initially separate components. During a dispensing operation, the tubes are collapsed to direct the components through a static mixer where the components are mixed for application directly to a work site.

2. Description of the Related Art

A variety of materials are made of two or more initially separate components that are preferably not mixed until immediately prior to use. Examples of such materials include epoxy adhesives, sealants and coatings used in the construction industry, and dental materials such as dental restoratives, adhesives and impressioning materials. In many instances, such two-component materials may unduly cure, harden or become otherwise unsatisfactory for use if mixed too far in advance of the actual time that the material is applied to the work site.

U.S. Pat. No. 4,538,920, assigned to the assignee of the present invention, describes a dispensing device for mixing and dispensing material made of two initially separate components. The device described in U.S. Pat. No. 4,538,920 includes a syringe having side-by-side parallel internal chambers and a pair of plungers to force the contents of the chambers through respective outlet passages and subsequently through a static mixing element carried within an exit conduit. The static mixing element intimately mixes the components to form a homogeneous mass that rapidly polymerizes following expulsion from an outlet of the exit conduit.

A double-barreled epoxy injection gun is described in U.S. Pat. Nos. 5,184,757 and 5,161,715 and includes separate barrels that each receive a sausage-shaped foil pack containing one component of a two-component mixture. The gun described in U.S. Pat. Nos. 5,184,757 and 5,161,715 includes a piston in each barrel, and the piston is advanced to crush the foil packs and thereby extrude the components.

U.S. Pat. No. 3,323,682 describes a cartridge for a single-barrel gun-type dispenser, and the cartridge has an outer shell containing a side-by-side pair of semi-cylindrical tubes. The tubes are made of a flexible material such as a plastic film, and include spouts that dispense components in two, spaced apart streams as the tubes are collapsed. The cartridge shown in U.S. Pat. No. 3,323,682 includes a rear plug that slides along the inner surface of the shell and bears against the collapsible tubes to expel the components.

SUMMARY OF THE INVENTION

The present invention is directed toward an assembly for dispensing material made of two or more components. The assembly comprises a first tube having a first chamber for receiving a first component. The first tube includes a first collapsible wall portion and a relatively rigid first end piece connected to the first collapsible wall portion. The first end piece includes an outlet port in communication with the first chamber. The assembly also includes a second tube having a second chamber for receiving a second component. The second tube includes a second collapsible wall portion and a relatively rigid second end piece connected to the second collapsible wall portion. The second end piece includes an outlet port in communication with the second chamber. The first tube and the second tube are connected to each other and oriented in side-by-side relation such that the first end piece and the second end piece remain next to each other as the first wall portion and the second wall portion are collapsed.

The assembly of the present invention is advantageous in that the relatively rigid end pieces provide a means for convenient handling of the assembly before use, and also when placed in a dispensing applicator during a dispensing operation. The relatively rigid end pieces further provide fixed structure for the outlet ports, and enable a manifold to be easily and securely fixed to the tubes when desired. When the relatively rigid end pieces are connected together, the end pieces retain the two tubes together as a single unit, the need for an outer shell or other packaging is eliminated.

BRIEF DESCRIPTION OF THE DRAWINGS

FIG. 6 is a view somewhat similar to FIG. 1 but in accordance with yet another embodiment of the invention; and FIG. 7 is an enlarged cross-sectional view taken along lines 7—7 of FIG. 6.

DETAILED DESCRIPTION OF THE PREFERRED EMBODIMENTS

Figure 1:
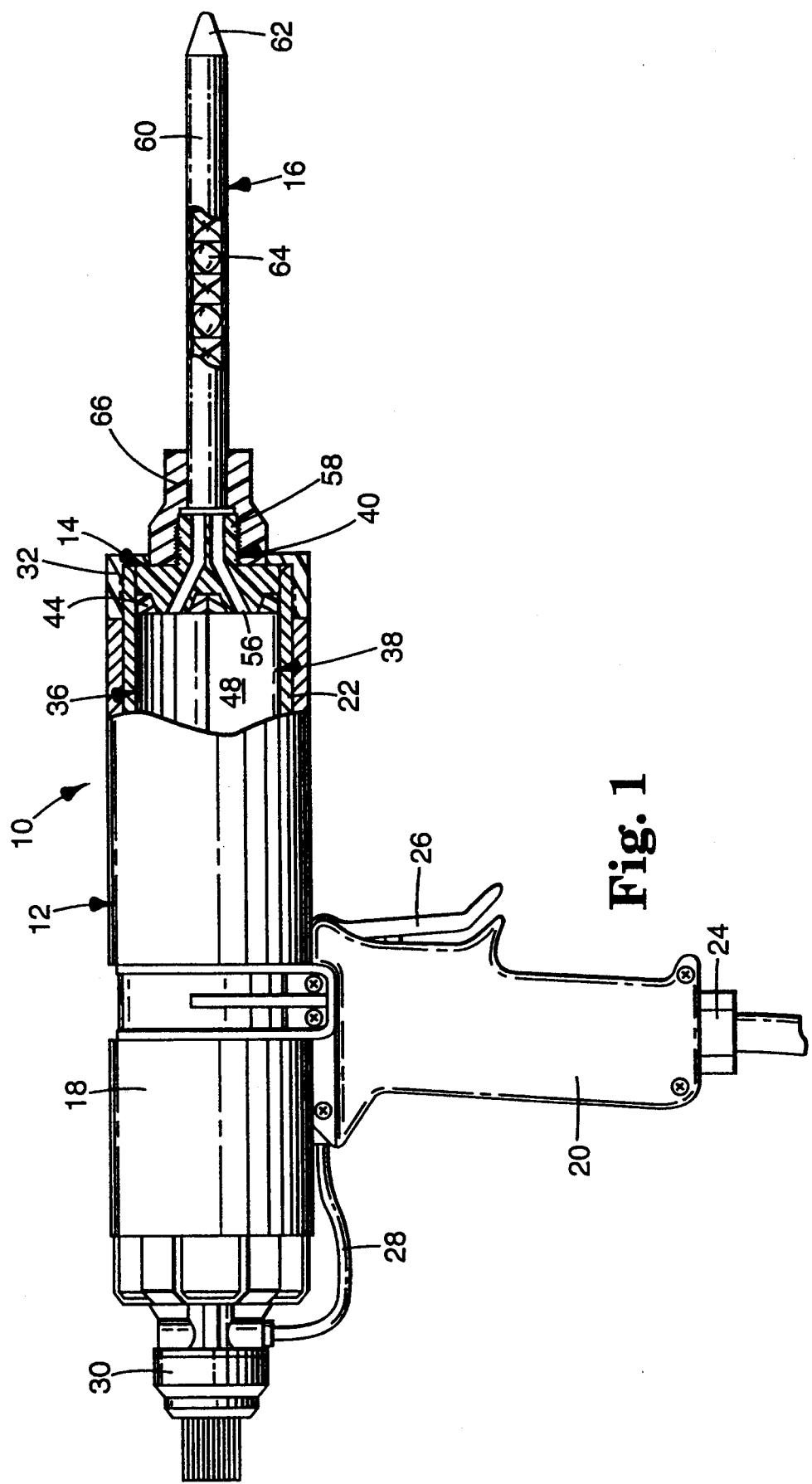
FIG. 1 is a side elevational view with parts broken away in section of a dispensing system that includes a dual collapsible tube dispensing assembly constructed according to the present invention.

A system for dispensing mixtures made of two initially separate components according to one embodiment of the invention is shown in FIGS. 1–4 and is broadly designated by the numeral 10 in FIG. 1. In brief, the system 10 includes an applicator 12 (FIG. 1), a collapsible tube mixing and dispensing assembly 14 (FIG. 2) and a static mixer 16 (FIG. 1).

In more detail, the applicator 12 includes a pistol-shaped housing 18 having a depending handle 20 and a single cylindrical barrel 22. The bottom of the handle 20 carries a fitting 24 that is adapted to be releasably connected to an air hose providing a source of pressurized air. The handle 20 also includes a trigger-style, normally-off air valve 26 for controlling the flow rate of air that passes through sections of tubing 28 extending from the fitting 24 to a pressurized air relief valve 30 located at the rear of the housing 18.

The pressurized air relief valve 30 provides adjustment of the amount of air pressure in the barrel 22 downstream of the relief valve 30. Pressurized air enters the barrel 22 from the relief valve 30 through six ports located at the rear of the barrel 22.

The applicator 12 also includes a cap 32 having a central orifice. The cap 32 has a coupling that comprises internal threads for matingly connecting with external threads located on a front end portion of the barrel 22. An example of a suitable applicator is the Cox air applicator, model no. Mk.5b-AC, although other applicators are also suitable. The barrel 22 may optionally include an internal piston that is advanced by air pressure as the air valve 26 is depressed.

Figure 3:
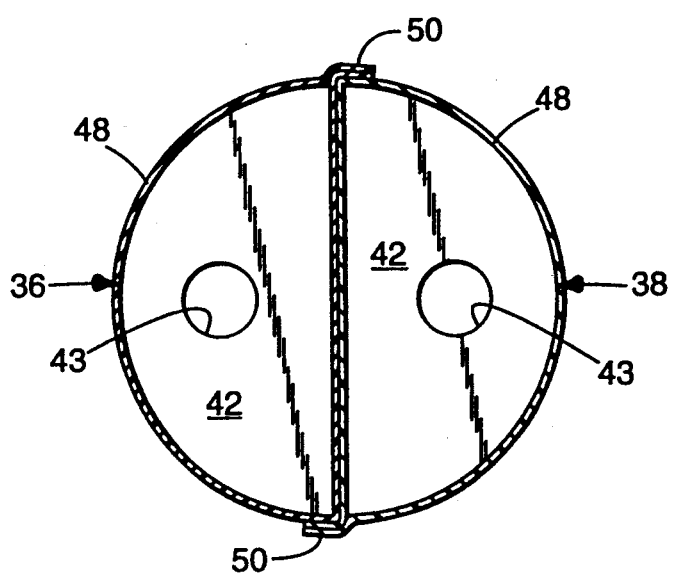
FIG. 3 is an enlarged cross-sectional view of the two tubes taken along lines 3—3 of FIG. 2.
Figure 4:
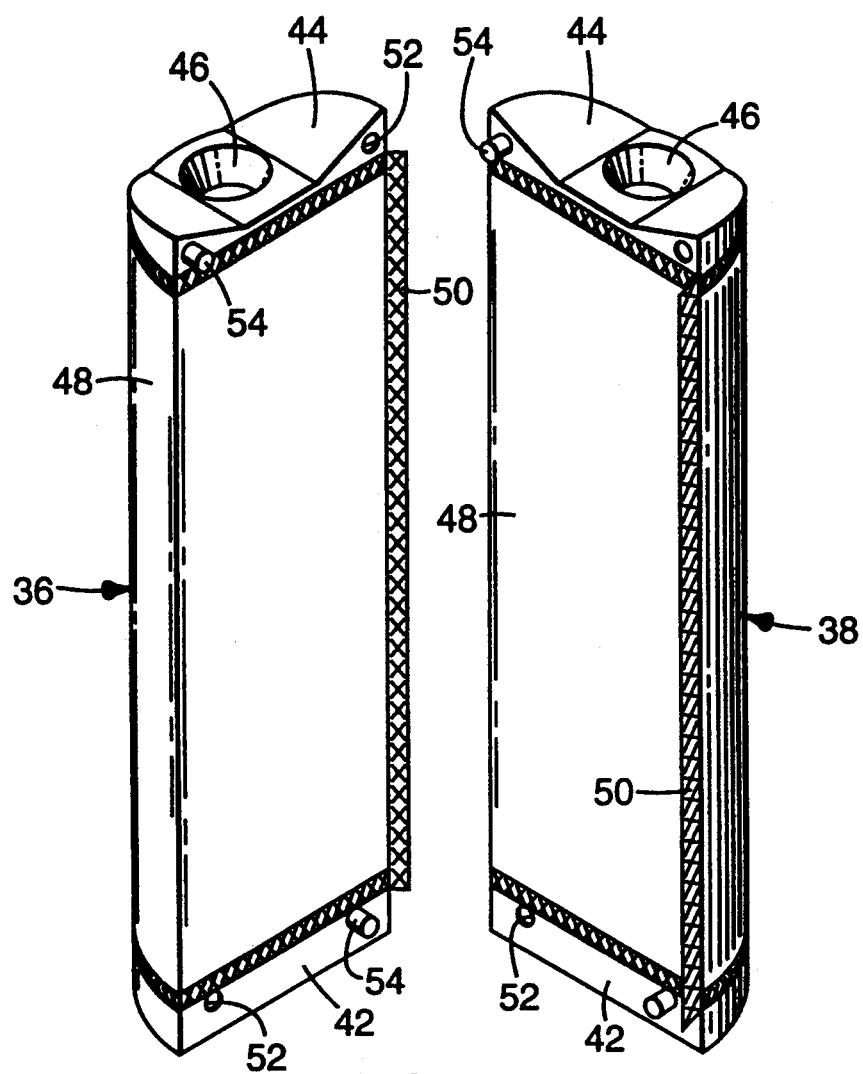
FIG. 4 is a perspective view of the two tubes illustrated in FIGS. 2 and 3 except that the tubes are detached from each other for illustrative purposes to show pin elements for coupling the tubes together.

The assembly 14 includes a first collapsible tube 36, a second collapsible tube 38 and a manifold 40. Each of the tubes 36, 38 has a generally right semi-cylindrical shape and includes a relatively rigid rear end piece 42 that initially has a hole 43 (FIG. 3). The holes 43 are provided for filling the tubes 36, 38 with the components to be dispensed, and are subsequently plugged or covered by tape.

The tube 36 includes a first, relatively rigid front end piece 44 having a chamfered recessed outlet port 46. Similarly, the tube 38 includes a second, relatively rigid front end piece 44 that also has a chamfered, recessed outlet port 46. The rear end pieces 42 and the front end pieces 44 are substantially semi-cylindrical in shape, except that the outer end of each front end piece 44 has a beveled, concave front wall when viewed in directions perpendicular to the longitudinal axes of the tubes 36, 38.

The tube 36 also includes a first collapsible wall portion that is made of a flexible film 48 having an initially rectangular shape. One edge portion of the film 48 is heat sealed to a forward peripheral edge section of the first rear end piece 42, and an opposite edge portion of the film 48 is heat sealed to a rear peripheral edge section of the first front end piece 44. Remaining edges of the film 48 are bonded together along a seam 50 to form a first sealed inner chamber that initially has a semi-cylindrical shape for receiving a first component of the mixture to be dispensed.

Likewise, the second tube 38 includes a second collapsible wall portion that is made of a flexible film 48. One edge portion of the film 48 of the second tube 38 is heat sealed to a forward peripheral section of the second rear end piece 42, and an opposite edge portion of the film 48 is heat sealed to a rear peripheral section of the second front end piece 44. Remaining edges of the film 48 of the second tube 38 are bonded together along a seam 50 to form a second sealed inner chamber that initially has a semi-cylindrical shape for receiving a second component of the mixture to be dispensed.

A presently preferred film 48 is made of a multiple-layer foil laminate material. An example of a suitable film 48 is from Ludlow Corporation of Lombard, Ill. and is a triple-layer laminate having a 48 gauge polyester outer layer, a 0.00035 in. (0.01 mm) thick aluminum (type 1145) middle layer and a 0.003 in. (0.08 mm) thick linear low density polyethylene (type 11513) inner layer, and between each adjacent pair of layers is a thermosetting adhesive (W-01-978) applied at a rate of 0.816 lbs. per 1000 sq. ft. (4 g/m$^2$) to secure the layers together. The end pieces 42, 44 are substantially more rigid (i.e., have a greater modulus of elasticity) than the films 48, are preferably injection molded and made of low density polyethylene.

Each of the end pieces 42, 44 has a pair of recesses 52 on its flat edge that face the flat edge of the other respective end piece 42, 44. Metal cylindrical pin elements 54 are securely affixed in half of the recesses 52 by pressing the pin elements 54 in place such that about one-half of the length of each pin element 54 protrudes from the corresponding end piece 42, 44. The remaining recesses 52 have a slightly larger diameter so as to releasably receive the pin elements 54 from the opposing tube 36, 38.

The pin elements 54 and the recesses 52 provide a means for interconnecting the tubes 36, 38 during a dispensing operation or, if desired, during preliminary handling of the assembly 14. When the tubes 36, 38 are so interconnected, the pair of rear end pieces 42 combine in abutted relationship to form a united cylindrical shape, while the front end pieces 44 combine an abutted relationship to form a generally cylindrical shape, except that the beveled front walls of the front end pieces 44 combine to present a united beveled cavity along the front of the tubes 36, 38 as can be observed in FIG. 3.

The manifold 40 has a rear convex beveled surface with a shape that matches the concave beveled cavity formed by the front walls of the front end pieces 44 when the tubes 36, 38 are interconnected. The manifold 40 also includes a pair of spaced apart, rearwardly extending, protruding inlet ports 56 (FIG. 1) having a chamfered shape that matches the chamfered shape of the recessed outlet ports 46 of the tubes 36, 38.

The front end of the manifold 40 includes a forwardly extending neck 58 having external circumscribing threads. A pair of separate passageways extend from respective inlet ports 56 and through the neck 58, and terminate at the front end of the neck 58 at outlet orifices that are spaced apart from each other.

The static mixer 16 includes an exit conduit 60 having a front dispensing outlet 62. A static mixing element 64 is received in the exit conduit 60, and includes a plurality of counter-rotated "bow-tie" or auger-like mixing blades of the type described in U.S. Pat. No. 4,538,920. The static mixing element 64 successively subdivides, rotates, and recombines incoming streams of the components to convert the components to a homogeneous, well-mixed material. The rear end of the exit conduit 60 is flared to engage a nut 66 that threadably connects with the external threads of the neck 58 of the manifold 40.

Figure 2:
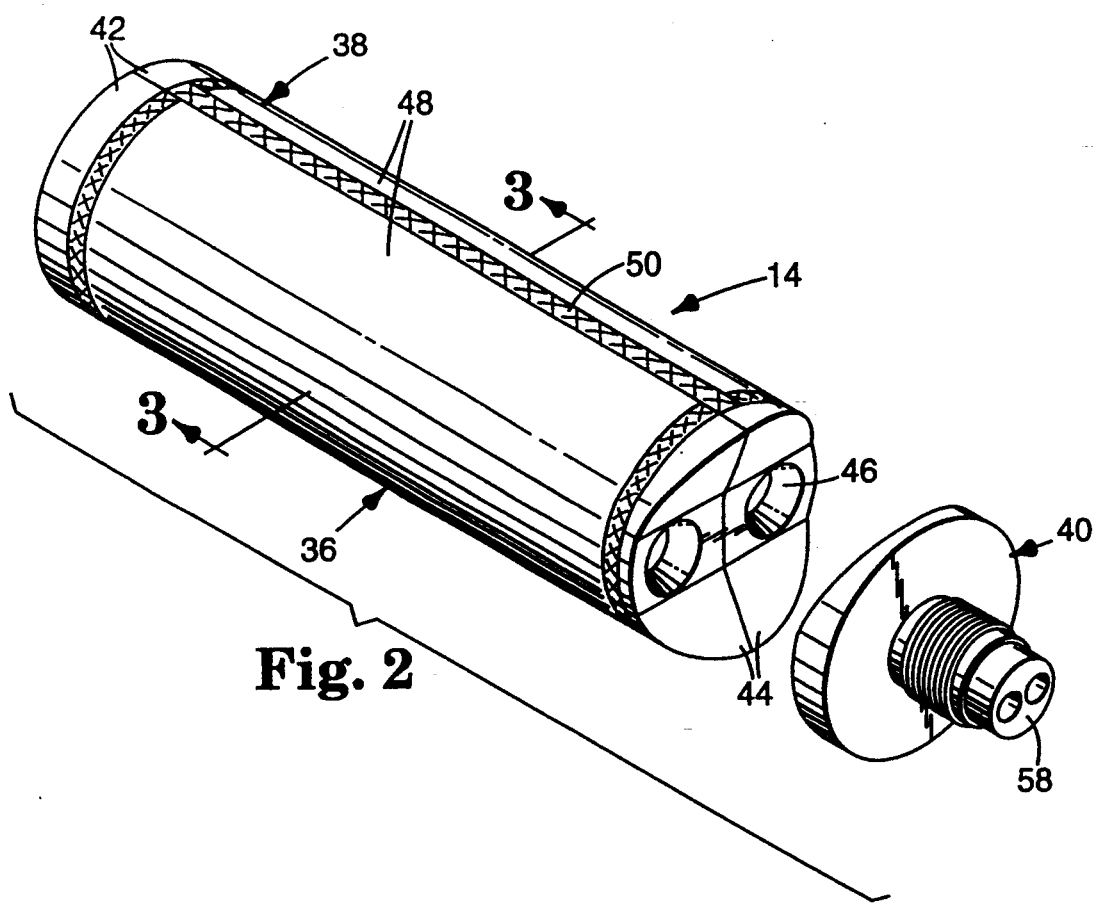
FIG. 2 is an enlarged perspective view of two tubes and a manifold of the assembly of FIG. 1, with the manifold shown as separated from the tubes for illustrative purposes.

In use, the tubes 36, 38 are connected together by the pins 54 and recesses 52 to form a united, substantially cylindrical unit. (If desired, the tubes 36, 38 may first be separately or together warmed in a preheater or by other means to enhance physical characteristics of the components therein and/or the mixed material ultimately dispensed.) Next, the connected-together tubes 36, 38 are placed in the barrel 22 of the applicator 12. The flexibility of the films 48 enable the seams 50 to be readily folded over adjacent portions of the films 48 as shown in FIGS. 2 and 3 and thereby tucked within the barrel 22 as the tubes 36, 38 are received in the latter.

The manifold 40 is then placed over the coupled-together front end pieces 44 in such a fashion that the rear convex surface of the manifold 40 mates with the united beveled cavity of the front end pieces 44 and the inlet ports 56 are received in the outlet ports 46 as shown in FIG. 1. The protruding inlet ports 56 and the protruding convex surface of the manifold 40 function to align the manifold 40 to the tubes 36, 38 in a certain rotative position relative to the longitudinal axes of the tubes 36, 38, so that the outlet ports 46 are placed in a position to communicate with the inlet ports 56. Next, the cap 32 is placed over the manifold 40 with the neck 58 of the manifold 40 protruding through the orifice of the cap 32. The cap 32 is then turned to threadedly secure the cap 32 to the barrel 22 and thereby releasably retain the tubes 36, 38 and the manifold 40 in the barrel 22.

Subsequently, the nut 66 of the static mixer 16 is threaded onto the neck 58 of the manifold 40 in order to connect the static mixer 16 to the assembly 14. The fitting 24 is coupled to the air hose providing pressurized air.

To dispense material, the trigger of the air valve 26 is depressed to admit air into the rear of the barrel 22. Air pressure on the rear end pieces 42 of the tubes 36, 38 urges the rear end pieces 42 in a forwardly direction toward the front end pieces 44, causing the films 48 to collapse in accordion-like fashion. As the tubes 36, 38 collapse, the components in each tube are directed through the separate passageways of the manifold 40 and then into the static mixer 16, whereupon the components are mixed and subsequently dispensed through the outlet 62 to the work site. The coupled-together rear end pieces 42 facilitate dispensing of equal quantities of components from the tubes 36, 38 as the tubes 36, 38 are collapsed.

If components remain in the tubes 36, 38 after completion of a dispensing operation, the static mixer 16 is left coupled to the manifold 40 to provide a seal. Immediately before the next dispensing operation, the static mixer 16 is disposed of and a new static mixer is provided in its place. If the contents of the tubes 36, 38 are exhausted after completion of a dispensing operation, the manifold 40 is cleaned for reuse at a subsequent time. As an alternative construction, the manifold 40 may be formed integrally with the static mixer 16, such that the entire unit of the manifold and static mixer is disposed of after use.

The pin element 54 of each front end piece 44 is positioned a certain distance away from the recess 52 located on the same front end piece 44, and such distance is greater than the distance between the pin element 54 and the recess 52 of each rear end piece 42. As a consequence, the front end piece 44 of the first tube 36 can only be coupled to the front end piece 44 of the second tube 38, and cannot be inadvertently coupled in an incorrect, opposite orientation fashion to the rear end piece 42 of the second tube 38. If desired, the distances between the pin elements 54 and the recesses 52 may be altered in certain instances, or the cylindrical configurations of the pin elements 54 and recesses 52 may be changed to other matching shapes such as pyramidal or the like, to ensure that only certain tubes containing specified components are coupled together for use.

Figure 5:
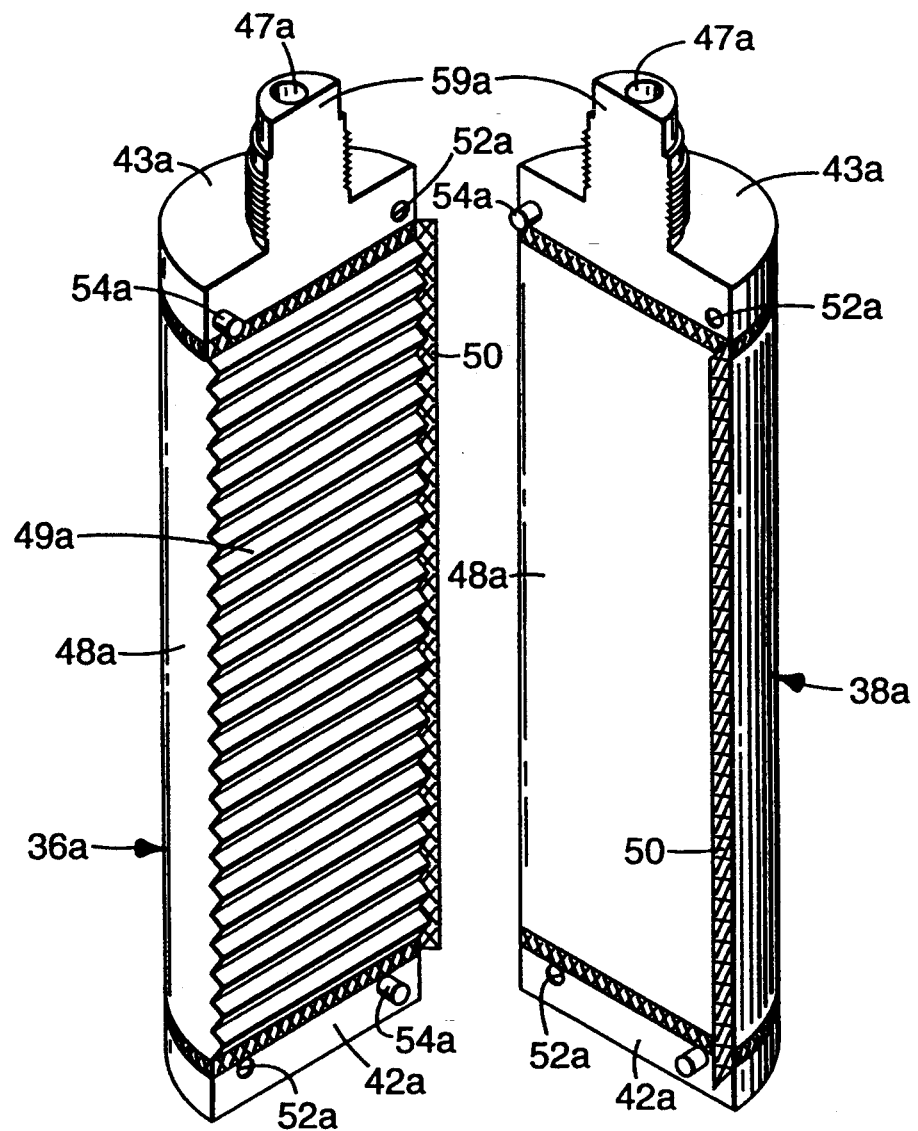
FIG. 5 is a perspective view somewhat similar to FIG. 4 but in accordance with another embodiment of the invention.

The embodiment of the invention that is illustrated in FIG. 5 is somewhat similar to the embodiment shown in FIGS. 1–4, in that a first collapsible tube 36a and a second collapsible tube 38a each have internal chambers for containing a first and second component respectively to be dispensed and mixed together. Each of the tubes 36a, 38a initially have a generally right semi-cylindrical shape and include a relatively rigid end piece 42a, a pin element 54a and a recess 52a identical to the end piece 42, pin element 54 and recess 52 described above.

The first tube 36a includes a collapsible wall portion made of a flexible film 48a identical to the film 48. However, a section of the film 48a of the tube 36a is bonded to a thin, foldable plate 49a that contacts the film 48a of the second tube 38a when the tubes 36a, 38a are assembled. The plate 49a is made of a 0.03 in. thick rigid material made of, e.g., plastic or metal that is scored to facilitate folding along reference axes perpendicular to the longitudinal axis of the tube 36a.

The foldable plate 49a serves as a collapsible divider wall to facilitate dispensing of substantially equal quantities of components from the chambers of the tubes 36a, 38a. For example, if the two components have substantially different viscosities, the component having the lower viscosity will present more resistance in flowing through the static mixer 16 than the other component. In such an instance, the plate 49a hinders the film 48a of the tube containing the component of a lower viscosity from bulging laterally into areas originally occupied by the tube containing the higher viscosity component. If desired, a second foldable plate similar to plate 49a may also be affixed to a section of the film 48a of the tube 38a in opposed, facing relation to the plate 49a of the first tube 36a.

Each of the tubes 36a, 38a includes a front end piece 43a having an outlet port 47a in communication with the chamber of the corresponding tube 36a, 38a. The front end pieces 43a are releasably coupled together by pins 54a and recesses 52a. A rear peripheral section of each front end piece 43a is sealed to the film 48a of the corresponding tube 36a, 38a.

Each of the front end pieces 43a includes a half-neck section 59a. When the tubes 36a, 38a are coupled together, the half-neck sections 59a abut each other and combine to form a configuration similar to the configuration of neck 58 in FIGS. 1–2, in order to releasably receive in threaded fashion a nut of a static mixer similar to the nut 66 of static mixer 16 illustrated in FIG. 1.

The embodiment illustrated in FIGS. 6–7 is also somewhat similar to the embodiment shown in FIGS. 1–4. With the exception of the differences described below, the elements in FIGS. 6–7 and FIGS. 1–4 that bear identical numerals are the same, and hence a detailed description of such elements will not be repeated.

Applicator 12b in FIGS. 6–7 has a fixed, rigid dividing wall member 23b that is integral with and extends horizontally between opposed sides of a cylindrical barrel 22b. Collapsible tubes 36b, 38b are substantially identical to the collapsible tubes 36, 38 described in connection with FIGS. 1–4, but the tubes 36b, 38b are slightly spaced apart in order to be received along opposite sides of the dividing wall member 23b in straddling relation. The flat, facing sides of the films 48b of the tubes 36b, 38b engage opposite sides of the dividing wall member 23b, and the forwardmost end of the dividing wall member 23b is located directly adjacent the rearwardly facing side of front end pieces 44b (see FIG. 6) when the tubes 36b, 38b are received in the applicator 12b.

The applicator 12b has dual pistons 13b that are connected together for simultaneous advancement or retraction by a linking member (not shown). When the air valve 26 is depressed, the pistons 13b simultaneously advance to collapse the tubes 36b, 38b. The pistons 13b are manually retracted by a lever (not shown) protruding laterally from the side of the applicator 12b.

During a dispensing operation, the dividing wall member 23b assists in retaining uncollapsed portions of the tubes 36b, 38b in a generally right semi-cylindrical shape, so that both tubes 36b, 38b collapse in simultaneous, similar fashion and do not lean or bulge laterally in a direction transverse to the direction of advancement of the pistons 13b. The dividing wall member is particularly useful where the components in the chambers of the tubes 36b, 38b have different viscosities.

While the foregoing embodiments have been described in connection with a pneumatic applicator, it is to be understood in this regard that the invention is also useful with an applicator having pistons that are advanced by a manual mechanism such as a ratchet assembly, or by a toggled plate assembly. The scope of the invention should not be limited to the specific embodiments illustrated in the drawings and described above.

I claim:

1. An assembly for use in a single elongated barrel of an applicator and for dispensing materials made of two or more components comprising:
   a first tube having a first chamber for receiving a first component, said first tube including a first collapsible wall portion and a separate relatively rigid first end piece connected to said first collapsible wall portion, said first end piece including an outlet port in communication with said first chamber; and
   a second tube having a second chamber for receiving a second component, said second tube including a second collapsible wall portion and a separate relatively rigid second end piece connected to said second collapsible wall portion, said second end piece including an outlet port in communication with said second chamber, said first tube and said second tube being connected to one another and oriented in side-by-side relation and together forming an elongated, generally cylindrical shape, such that said first end piece and said second end piece remain next to each other as said first wall portion and said second wall portion are collapsed in a direction along the longitudinal axis of said generally cylindrical shape.

2. The assembly of claim 1, including a manifold having a pair of inlet ports, and a coupling for coupling said manifold to said first tube and said second tube such that said inlet ports of said manifold are in communication with said outlet ports of said first end piece and said second end piece.

3. The assembly of claim 2, and including an applicator having a barrel and a cap, wherein said first tube and said second tube are received in said barrel, and wherein said coupling includes structure for connecting said cap to said barrel.

4. The assembly of claim 2, wherein said first tube and said second tube have parallel longitudinal axes, and wherein said manifold includes means for aligning said manifold in a certain rotative position relative to said first tube and said second tube in directions about said axes.

5. The assembly of claim 4, wherein said first end piece and said second end piece include a cavity, and wherein said means comprises a convex surface having a configuration complemental to said cavity.

6. The assembly of claim 1, wherein at least one of said tubes includes a protruding element for connecting said first tube to said second tube.

7. The assembly of claim 6, wherein said element releasably connects said first tube to said second tube.

8. The assembly of claim 6, wherein said element comprises a pin that is fixedly secured to said first tube and wherein said second tube has a hole for releasably receiving said pin.

9. The assembly of claim 1, wherein said first end piece and said second end piece each include a half-neck section, and wherein said half-neck sections are connected to each other when said first tube and said second tube are connected to each other.

10. The assembly of claim 9, wherein said half-neck sections include threaded portions for coupling to a static mixer.

11. An assembly for dispensing materials made of two or more components comprising:
   a first tube having a first chamber for receiving a first component, said first tube including a first collapsible wall portion and a separate relatively rigid first end piece connected to said first collapsible wall portion, said first end piece including an outlet port in communication with said first chamber;
   a second tube having a second chamber for receiving a second component, said second tube including a second collapsible wall portion and a separate relatively rigid second end piece connected to said second collapsible wall portion, said second end piece including an outlet port in communication with said second chamber, said first tube and said second tube being connected to one another and oriented in side-by-side relation such that said first end piece and said second end piece remain next to each other as said first wall portion and said second wall are collapsed;
   a manifold having a pair of inlet ports;
   a coupling for coupling said manifold to said first tube and said second tube such that said inlet ports of said manifold are in communication with said outlet of said first end piece and said second end piece; and
   an applicator having a barrel and a cap, wherein said first tube and said second tube are received in said barrel, wherein said coupling includes structure for connecting said cap to said barrel, wherein said cap includes an orifice, and wherein said manifold includes a neck that extends through said orifice.

* * * * *